United States Patent [19]
Li

[11] Patent Number: 5,677,284
[45] Date of Patent: Oct. 14, 1997

[54] CHARGED COLLAGEN PARTICLE-BASED DELIVERY MATRIX

[75] Inventor: Shu-Tung Li, Oakland, N.J.

[73] Assignee: ReGen Biologics, Inc., Menlo Park, Calif.

[21] Appl. No.: 467,578

[22] Filed: Jun. 6, 1995

[51] Int. Cl.$^6$ .................. A61K 38/00; A61K 38/17; A61F 13/00
[52] U.S. Cl. .................. 514/21; 514/801; 530/356; 424/422; 424/423; 424/484; 424/491
[58] Field of Search ............. 514/21, 801; 530/356; 424/422, 423, 484, 491

[56] References Cited

U.S. PATENT DOCUMENTS

| | | | |
|---|---|---|---|
| 4,394,370 | 7/1983 | Jefferies | 424/15 |
| 4,472,840 | 9/1984 | Jefferies | 530/356 |
| 4,539,716 | 9/1985 | Bell | 623/1 |
| 4,657,548 | 4/1987 | Nichols | 623/10 |
| 4,711,783 | 12/1987 | Huc et al. | 424/460 |
| 4,774,091 | 9/1988 | Yamahira et al. | 424/426 |
| 4,789,662 | 12/1988 | Thomas-Leurquin et al. | 514/21 |
| 4,846,835 | 7/1989 | Grande | 623/11 |
| 4,863,732 | 9/1989 | Nathan et al. | 424/95 |
| 5,196,185 | 3/1993 | Silver et al. | 424/45 |
| 5,206,028 | 4/1993 | Li | 424/484 |
| 5,460,962 | 10/1995 | Kemp | 435/238 |
| 5,532,217 | 7/1996 | Silver et al. | 514/21 |

OTHER PUBLICATIONS

Green et al, *Biochemistry Journal*, vol. 54, pp. 181–187, 1953.

Gustavson, *Arkiv För Kemi*, vol. 17, No. 55, pp. 541–550, Feb. 8, 1961.

Bradley et al., "Some Mechanical Property Considerations of Reconstituted Collagen For Drug Release Supports" Biomat., Med. Dev., Art. Org., 5(2), 159–175 (1977).

Cook et al, "In Vivo Evaluation of Recombinant Human Osteogenic Protein (rhOP-1) Implants As a Bone Graft Substitute for Spinal Fusions", Spine 19:1655–1663, 1994.

Fraenkel–Conrat et al., "Esterification of Protein With Alcohols of Low Molecular Weight", Journal B. C. 16:259–268, 1945.

Green et al., "Acetylation of Collagen", Biochemistry Journal, 54:181–187, 1953.

Gustavson et al., "Some Reactions of Succinylated Collagen", Arkiv Kemi 11:541–550, 1961.

Murray et al., "Collagen Shield Heparin Delivery for Prevention of Postoperative Fibrin", Arch Ophthalmol 108:104–106, 1990.

Nakano et al., "The Effect of Charges on Permeabilities of Drugs through Collagen Membranes", Chem. Pharm. Bull. 24(10)2345–2349, 1976.

Schwartz et al., "Collagen Shield Delivery of Amphotericin B", American Journal of Ophthalmology 109:701–704, 1990.

Weiner et al., "Liposome–Collagen Gel Matrix: A Novel Sustained Drug Delivery System", Journal of Pharm. Sciences 74:922–925, 1985.

Yasko et al., "The Healing of Segmental Bone Defects, Induced by Recombinant Human Bone Morphogenetic Protein (rhBMP-2)", The Journal of Bone and Joint Surgery 74–A, No. 5, 659–670, 1992.

*Primary Examiner*—Cecilia J. Tsang
*Assistant Examiner*—Abdel A. Mohamed
*Attorney, Agent, or Firm*—Fish & Richardson P.C.

[57] ABSTRACT

A collagen-based delivery matrix including collagen particles, wherein each of the particles has a diameter between 5 μm and 850 μm and, when suspended in an aqueous solution at a pH of about 7.0, has a net charge density between −20 moles/mole collagen and −500 moles/mole collagen, or between +20 moles/mole collagen and +250 moles/mole collagen. Also disclosed are methods of preparing and using such a delivery matrix.

22 Claims, No Drawings

CHARGED COLLAGEN PARTICLE-BASED DELIVERY MATRIX

BACKGROUND OF THE INVENTION

This invention relates generally to the delivery of therapeutic agents.

In general, a water soluble bioactive agent can be incorporated into a water soluble/swellable collagen delivery matrix with ease. This can be achieved by mixing the water soluble bioactive agent with a collagen preparation, co-precipitating the agent with collagen, entrapping the agent into a collagen matrix, or entangling the agent with collagen fibers. Because of the versatility of collagen as a delivery vehicle, particularly fiber-forming collagens such as type I collagen, many biologically active agents including live cells can be incorporated into the collagen matrix in a controllable manner.

Despite the useful properties of collagen for delivery applications, methods for more effectively and more efficiently delivering bioactive agents using insoluble collagen particle matrices remain to be developed.

SUMMARY OF THE INVENTION

An aspect of the present invention relates to a collagen-based delivery matrix. The matrix includes collagen particles (e.g., prepared from type I collagen), each of which has a diameter between 5 μm and 850 μm (preferably, between 15 μm and 600 μm) and, when suspended in an aqueous solution at a pH of about 7.0 (i.e., pH 6.5–7.8), has a net negative charge density between −20 moles/mole collagen and −500 moles/mole collagen (preferably, −40 moles/mole collagen to −400 moles/mole collagen; and more preferably, −100 moles/mole collagen to −300 moles/mole collagen) or a net positive charge density between +20 moles/mole collagen and +250 moles/mole collagen (preferably, +50 moles/mole collagen to +200 moles/mole collagen; and more preferably, +100 moles/mole collagen to +160 moles/mole collagen). The diameter of a collagen particle recited in this disclosure refers to the greatest dimension of the particle after it has been air dried, freeze dried, or vacuum dried (i.e., under the conditions set forth in Example 1, Preparation of Collagen Particles, E. and F., below or equivalents thereof). Also note that the charge density value of a collagen particle recited herein is an averaged number calculated based on a formula set forth in Example 1, Alteration of Net Charge Density to −40—−70 moles/mole, below.

Another aspect of this invention relates to a method of preparing collagen particles for a collagen delivery matrix. The method includes the steps of first fragmenting (e.g., via grinding or cutting) a collagen preparation (e.g., pure or substantially pure collagen, e.g., ≧90% weight of collagen per dry weight of purified material as indicated by a hydroxyproline content analysis of the purified collagen material) to form collagen particles; and next chemically modifying the particles (e.g., deamidation, acetylation, succinylation, deguanidination, methylation, or a combination thereof) so that each of the particles, when suspended in an aqueous solution at a pH of about 7.0 (i.e., pH 6.5–7.8), has a net charge density between −20 moles/mole collagen and −500 moles/mole collagen or between +20 moles/mole collagen and +250 moles/mole collagen. It is desirable that either before or after the modifying step only particles which have diameters between 5 μm and 850 μm (preferably, between 15 μm and 600 μm) be selected, e.g., via sieving.

Also within the scope of this invention is a method of using collagen particles each of which has a diameter between 5 μm and 850 μm (preferably, between 15 μm and 600 μm) and, when suspended in an aqueous solution at a pH of about 7.0 (i.e., pH 6.5–7.8), has a net charge density between −20 moles/mole collagen and −500 moles/mole collagen or between +20 moles/mole collagen and +250 moles/mole collagen. The method includes the step of mixing three components, i.e., a bioactive agent, an aqueous solution, and the just-mentioned collagen particles, to form a paste-like material. While it is preferred that the solution have a pH of about 7.0, a higher or lower pH may be used under certain circumstances. In general, any two of the three components can be mixed first before adding the third component. Alternatively, all three components can be blended together at the same time. The paste-like material can be further processed (e.g., fabrication into a proper matrix form), if necessary, before being delivered into or onto a subject (i.e., a mammal, such as a human patient) to be treated with the bioactive agent. The delivery can be effected either with a syringe, a cannula, or a catheter; or by surgical implantation.

The bioactive agents which can be administered to a subject using the collagen-based delivery matrix described above include, but are not limited to, growth factors (such as transforming growth factor-β, epidermal growth factor, insulin-like growth factor, platelet derived growth factor, fibroblast growth factor, and bone morphogenetic protein), prostaglandin, thrombin, macromolecules (e.g., cell adhesive proteins such as laminin, fibronectin and chondronectin, polysaccharide such as glycosaminoglycan, glycoprotein, and collagens such as type I collagen through type XIV collagen), live cells, allogeneic bone chips, autogenous bone chips, tricalcium phosphate, hydroxyapatite, calcium carbonate, and bioglass.

The collagen particle matrix of this invention has a high capacity of absorbing a bioactive agent-containing aqueous solution as measured by a method described in Example 1, last paragraph, below.

Other features or advantages of the present invention will be apparent from the following detailed description of several embodiments, and also from the appending claims.

DETAILED DESCRIPTION OF THE INVENTION

The collagen particle delivery matrix in accordance with the present invention is comprised of highly hydrophilic, insoluble collagen particulates with diameters between 5 μm and 850 μm, and of a net charge density in the range of from −20 moles/mole collagen to −500 moles/mole collagen or from +20 moles/mole collagen to +250 moles/mole collagen when suspended in an aqueous solution at a pH value of about 7.0 (i.e., 6.5–7.8).

As an example, the collagen-based delivery matrix of this invention can be prepared from the native type I collagen. The type I collagen molecule has about 250 positively charged groups (ε-amino groups of lysines and hydroxylysines each having a pK of greater than pH 9, and guanidino groups of arginines having a pK of greater than pH 12), and about 250 negatively charged groups (β-carboxyl groups of aspartic acids and γ-carboxyl groups of glutamic acids, each having a pK of less than pH 5). As a result, at a pH of about 7.0 (i.e., 6.5–7.8) the collagen molecule is electrically neutral and as a result, its particles do not form an effective cohesive matrix.

To obtain a collagen-based delivery matrix with collagen particles each having a desirable net negative charge density at a pH of about 7.0 (i.e., 6.5–7.8), the ε-amino groups of lysines and hydroxylysines of the collagen particles can be subjected to chemical modification reactions, such as acetylation with acetic anhydride to convert the positively charged ε-amino groups to neutral acetyl groups. Since there are about 100 ε-amino groups per type I collagen molecule, the net charge density of a fully acetylated collagen becomes −100 moles/mole collagen at a pH of about 7.0 (i.e., 6.5–7.8), and the collagen becomes more hydrophilic and absorbs more water (swells) as a result of the repulsive electrostatic interactions of the negatively charged carboxyl groups. To increase the degree of hydrophilicity (swelling capability) further, the ε-amino groups of lysines and hydroxylysines can be converted into carboxyl groups (charge reversion) by succinylation using succinic anhydride. The net charge density of a fully succinylated collagen therefore is about −200 moles/mole collagen. An even higher degree of hydrophilicity (or net charge density) of collagen can be obtained by sequential chemical modifications, e.g., by first converting all the guanidino groups of arginines in collagen to amino groups (converting arginine into ornithine) by a deguanidination reaction in the presence of hypobromite in alkaline conditions, followed by succinylation using succinic anhydride. The net charge density resulting from these sequential modifications is about −500 moles/mole collagen at a pH of about 7.0 (i.e., 6.5–7.8).

Collagen particles with a net positive charge density can also be made by modifying the carboxyl groups such as via an esterification reaction with methyl alcohol to convert the carboxyl groups to methyl ester groups. A completely methylated collagen has a net charge density of about +250 moles/mole collagen. Like the negatively charged collagen, the positively charged collagen has a higher degree of hydrophilicity and swells at a pH of about 7.0 (i.e., 6.5–7.8) due to repulsive charge interactions between the amino and guanidino groups of lysines, hydroxylysines and arginines.

If necessary, a polyanionic polymer such as alginic acid or polyglutamic acid may be covalently bound to the collagen particles using a crosslinking agent such as carbodiimide, forming amide bonds between the carboxyl groups of the polyanionic polymer and the amino groups of the collagen. By doing so, the net charge density of the collagen particles increases as a result of the increase of the average number of carboxyl groups per collagen molecule. It must be pointed out that incorporation of polyanionic polymer into the collagen matrix depends on the diameter of the polymer, and thus the diffusion rate of the polymer into the collagen matrix for effective coupling between the polymer and the collagen. Ineffective coupling will result in surface coupling which does not create significant matrix swelling. More effective incorporation may be achieved by performing the coupling reaction under matrix swelling conditions to facilitate polymer diffusion into the interior space of the collagen matrix such as at a pH of less than 4 or above 11.

Furthermore, a polycationic polymers such as polylysine, chitosan and the like may be covalently coupled with a collagen matrix, using carbodiimide as a crosslinking agent such that the amino groups of the polycations are linked to the carboxyl groups in the collagen. By doing so, the net charge density of the collagen particles increases with the increase of the average number of amino groups per collagen molecule.

To deliver a peptide or protein having a net positive charge, the collagen delivery matrix with a net negative charge is more desirable. The delivery matrix serves to bind the bioactive peptide or protein by electrostatic interactions, in addition to mechanical interactions such as entanglement and entrapment. On the other hand, to deliver a peptide or protein having a net negative charge, the delivery matrix with a net positive charge is more desirable. Further, depending on the diameter of the bioactive agent to be delivered, the extent of repulsive interactions (swelling) of the collagen molecules within the matrix can be controlled such that the optimal delivery condition of the matrix can be obtained to maximize the efficacy of the particular bioactive agent of interest. It is often desirable to first encapsulate the bioactive agent in a form of liposomes, microcapsules or impregnated into synthetic polymers by methods well known in the art as an additional means to control the rate of release of certain bioactive agents. In this particular case, the bioactive agent-containing liposomes, microcapsules or synthetic polymers may first be dispersed in an aqueous solution which is then mixed with the collagen delivery matrix to form a paste-like matrix for delivery.

When the bioactive agent to be delivered is an insoluble material such as bone chips or particles, bioglass or hydroxyapatite particles, these materials can be incorporated into the collagen particle delivery matrix by the cohesive mechanical forces exerted on these bioactive materials from the delivery matrix at a pH of about 7.0 (i.e.,6.5–7.8).

The particle diameter of the delivery matrix of the present invention is important. Dry collagen particles with diameters greater than 850 μm are generally ineffective in forming a cohesive paste-like matrix and, therefore, in their delivery capability. This is due to the reduction of surface areas of the large particles where inter-particle interactions are reduced. On the other hand, if the particle diameters are too small, for example less than 5 μm, the particles may be phagocytozed by the inflammatory cells in vivo or migrate out from the delivery site, thereby minimizing the residence time of the delivery matrix in situ and leading to a quick dissipation of the associated bioactive agents. For example, collagen particles greater than 850 μm tend to form a sand-like characteristics when hydrated, rather than form a cohesive paste-like substance.

The bioactive agent-containing collagen matrix can be delivered to the particular tissue or organ site by direct implantation, by use of a syringe, a cannula, or a catheter via percutaneous approach, or by an arthroscopically assisted surgery approach such that the paste-like material is delivered and conformed to the tissue or organ site of interest.

As an example, when type I collagen is used to prepare the delivery matrix of this invention, it can be obtained from any type I collagen-rich tissues, either from humans or animals. These tissues include, but are not limited to, skin, bone, tendon, and ligament. Animal tissues are preferred due to the ease of obtaining fresh tissues in large quantities under controlled conditions. The following procedures may be followed to prepare the type I collagen particle delivery matrix from tendon:

Tendon is first cleaned of fascia and extraneous tissues and minced. The minced tendon is extracted in a 1M NaCl, pH 7.0 to remove a small portion of the collagen molecules that are newly synthesized and have not yet been incorporated into the stable fibrils, as well as glycoproteins and proteoglycans that are associated with collagen through non-covalent interactions. Other salts such as potassium chloride and the like can be used as a substitute for sodium chloride.

Lipids that are associated with the cell membranes or collagenous tissues are removed by first extracting with detergents such as Triton X-100 (Sigma Chemical Co., St.

Louis, Mo.), followed by extracting with ether-ethanol mixtures. The concentration of Triton X-100 is usually about 2% to 4%, but is preferably about 3%. The preferred mixture of ether-ethanol is usually at about a 1:1 ratio (v/v). The period of extraction is usually from about 8 hours to about 96 hours, but is preferred from about 24 to 48 hours.

Further purification may be accomplished by extracting the tendon under acidic and basic conditions. Both acidic and basic extractions weaken the non-covalent intermolecular interactions, thus facilitating the release of non-covalently attached glycoproteins, glycosaminoglycans ("GAGs"), and other non-collagenous molecules.

The extraction of tendon under an alkaline condition is accomplished by treating the tendon with $Ca(OH)_2$, NaOH, or the like, at a pH between 12 to 13 for a period of 8 to 96 hours in the presence of a structure stabilizing salt such as $(NH_4)_2SO_4$, $Na_2SO_4$ and the like to minimize the potential risk of denaturing the collagen. Alkali treatment dissociates the non-crosslinked glycoproteins and GAGs from the collagen matrices, and also removes the residual lipid through saponification.

The acid extraction may be conducted at a pH below 3 in the presence of a structure stabilizing salt. Acids such as acetic acid, hydrochloric acid, or the like may be used. Like the alkaline extraction, the acid extraction removes non-crosslinked glycoproteins and GAGs.

The non-triple helical portions of the collagen molecule (telopeptides) are involved in intermolecular crosslinking formation. They are weak antigens and are susceptible to attack by proteases, such as pepsin, trypsin, and the like. Prolonged digestion with such proteases dissociates the fibrils into individual molecules. However, if the digestion process is properly controlled such that maximal telopeptides are removed without complete dissociation, the immunogenicity of the fibrils may be further reduced without significantly compromising the mechanical strength. For example, to isolate collagen monomers (unsuitable for use in a delivery matrix), the digestion of skin or tendon with pepsin is usually conducted at an enzyme:collagen ratio of about 1:10 (w/w) for about 24–96 hours below room temperature. On the other hand, collagen fibrils, which are suitable for use in a delivery matrix, can be obtained by limited pepsin digestion achieved at a ratio of about 1:200 (enzyme:collagen w/w) for about 10–48 hours at 4° C.

In an embodiment, the purified collagen is further processed to produce particle of appropriate diameters before any chemical modifications. For example, the purified collagen fibers are first air or vacuum dried and then subjected to cutting or grinding and sieving procedures to produce particles with diameters between 5 μm and 850 μm. Any commercial grinding machine may be used for this purpose. The grinding or cutting of fiber-based collagen materials, such as those prepared from tendon or skin, produces irregularly shaped fibrous particles of various diameters, which are then subjected to a size separation procedure to obtain particles of predetermined diameters. Commercial sieves of various mesh sizes are suitable for this size separation procedure.

Illustrative examples of chemical modifications which can be used to alter the net charge density of collagen particles are listed in the table below:

| Chemical modification | Net Charge Density† (moles/mole) |
| --- | --- |
| Deamidation[a] | −70 |
| Acetylation[b] | −100 |
| Succinylation[c] | −200 |
| Deguanidination[d] + Acetylation[b] | −250 |
| Deguanidination[d] + Succinylation[c] | −500 |
| Methylation[e] | +250 |
| Methylation[e] + Acetylation[b] | +150 |

†The values listed were measured at pH 7.4 and represent the maximal values which can be obtained by the modification(s) with dry collagen particles having diameters between 5 μm and 850 μm.
[a]Bowes, et al., Biochem. J. 43:365-372, 1948.
[b]Green, et al., Biochem. J. 54:181-187, 1953.
[c]Gustavson, Arkiv for Kemi 17:541-550, 1961.
[d]Bose et al., Archives of Biochem. and Biophys. 74:46, 1958.
[e]Fraenkel-Conrat, et al., J. Biol. Chem. 161:259-268, 1945.

Without further elaboration, it is believed that one skilled in the art can, based on the description herein, utilize the present invention to its fullest extent. The following specific embodiments are, therefore, to be construed as merely illustrative, and not limitative of the remainder of the disclosure in any way whatsoever. All publications cited herein are hereby incorporated by reference.

EXAMPLE 1

Preparation of Collagen Particles
A. Mechanical Disintegration
Bovine Achilles tendon was obtained from a USDA-approved slaughter house. The tissue was kept cold during the purification process except where specified to minimize bacteria contamination and tissue degradation.

The adhering tissues of carefully selected tendons were first scrapped off mechanically. The tendons were cut into fine pieces and washed in excess quantities (10 volumes) of cold water to remove residual blood proteins and water soluble materials.
B. Salt Extraction
The washed tendons were extracted in ten volumes of 5% NaCl, 0.1M phosphate buffer, pH 7.4 for 24 hours to remove salt soluble materials. The salt extracted tendons were repeatedly washed in about 10 volumes of water to remove the salt.
C. Lipid Extraction
The material was extracted in 3% Triton X-100 for 24 hours. The detergent was removed by extensive washing with water. The material was then extracted in 3–4 volumes of ether-ethanol (1:1 vol/vol) for 24 (±2) hours to further minimize the lipid content. The lipid extracted material was extensively washed in water to remove the ether and ethanol.
D. Acid and Base Extraction
The material was subjected to acid and base extractions to remove non-collagenous materials. Base extraction was conducted with 3–4 volumes of 0.1M NaOH at room temperature in the presence of 1.0M $Na_2SO_4$ for 24 (±2) hours with mild agitation. Following base extraction, the pH was neutralized with 0.1M HCl. The pH was then adjusted to 2.5 by adding concentrated lactic acid to a final concentration of 0.2M. The acid extraction was continued for 24 (±2) hours with agitation. The acid extracted collagen fibers were extensively washed with distilled water.
E. Coacervation
The partially swollen fibrillar material was then coacervated by adjusting the pH to its isoelectric point between pH 6.5 to 7.0 with 0.1M NaOH. The coacervated collagen fibers were harvested by filtration, and the filtered material was extensively washed with cold distilled water. The highly purified collagen (type I collagen) was freeze dried (first at −10° C., <200 µm Hg vacuum for 24 hours, and then at 20° C., <200 µm Hg vacuum for 24 hours) and stored at room temperature as dry fibers.

F. Grinding and Sieving

The purified collagen fiber material was first vacuum dried (at 20° C., <200 µm Hg vacuum for 24 hours) to remove the absorbed moisture during storage and then ground in a Thomas Wiley Mill (Thomas Scientific, Swedesboro, N.J.). The ground collagen particles were sieved between mesh size 40 (450 µm) and mesh size 400 (40 µm) to collect the particles with diameters between 40–450 µm.

Alteration of Net Charge Density to −40−−70 moles/mole

Ten grams of collagen particles thus obtained were deamidated in 1.1M NaOH solution in the presence of 1.0M $Na_2SO_4$ as a triple helical stabilizing salt for 24 hours at room temperature under constant agitation. The deamidated collagen fibers were extensively washed with deionized water pre-adjusted to about pH 5 to minimize the swelling. The deamidated, washed collagen fibers were collected and air dried.

The method for determining the net charge (Z) is based on applying the condition of electrical neutrality to both the charged protein molecules and to the intermolecular solvent. The net charge is calculated based on the following equation: $Z=\Gamma_{Cl}-\Gamma_{Na}$, where $\Gamma$ represents the excess of sodium or chloride ions in the intermolecular space (per collagen molecule) over the amount which would have been present if collagen had no polar residues. A typical $\Gamma$ is determined as follows.

A one-gram sample of vacuum dried collagen particles is equilibrated with an excess amount of 0.16M NaCl solution in the presence of radioactive sodium ($^{22}Na$) or chloride ($^{36}Cl$) for 24 hours at room temperature with shaking. A weighed aliquot of the supernatant is then taken to determine the moles of radioactivity per ml of solution. The wet collagen sample is then weighed into a polypropylene test tube, and the radioactivity is extracted for 24 hours with traceless solution. This solution is then assayed for radioactivity. Beta radiation is assayed using a liquid scintillation counter and gamma radiation is assayed using a gamma spectrometer. The weight of collagen is obtained by drying the reacted collagen sample over $P_2O_5$ for 72 hours. A $\Gamma$ is calculated according to the following formula.

$$\Gamma(\text{moles/mole})=[m^*/C^*-g_r/\rho]C\times M_c\times 10^{-3}/g_c$$

where $g_c$ and $g_r$ are the weights of collagen and solution, respectively, in the sample analyzed; $m^*$ is the amount of $^{22}Na$ or $^{36}C$ present; $C^*$ and $C$ represent the molal concentration of the $^{22}Na$ and $Na^+$ or $^{36}Cl$ and $Cl^-$ in the reaction solution at equilibrium. $M_c$ is the molecular weight of collagen, and $\rho$ is the density of the equilibrating solution.

The net charge of the deamidated collagen particles from various batches, determined by the above method, was found to range between −40 moles/mole to −70 moles/mole.

The average isoelectric point of the collagen particles was determined as follows: One gram of collagen sample was uniformly dispersed and homogenized in a 100 ml of 0.07M lactic acid solution, pH 2.5. A 0.5% $NH_4OH$ solution was slowly added to the dispersed collagen. The pH of the collagen dispersion was continuously monitored until a full separation of the phase occurred. The pH of the solution at full phase separation was taken as the estimated value of the average isoelectric point of the collagen preparation. The isoelectric point for the deamidated collagen particles from various batches was found to be in the range of from about pH 4.4 to about 5.0.

A one-gram sample of the vacuum dried collagen particles was weighed into a test tube, to which a phosphate buffered saline solution, pH 7.4 was slowly added. The test tube was reverted after each 0.25 ml of the solution was added. The saturation point was reached when the maximum amount of the solution was absorbed into the sample without a clear phase separation between the collagen particles and the solution when the test tube was reverted. The maximum volume of the solution absorbed without a phase separation was taken as the absorption capacity of the collagen delivery matrix, in units of gram solution per gram of dry collagen. The sample was found to have a solution absorption capacity of about 10 g solution per gram collagen.

EXAMPLE 2

Preparation of Collagen Particles

Collagen particles were prepared in a manner identical to that described in Example 1 above.

Alteration of Net Charge Density to −40−−100 moles/mole

Ten grams of collagen particles thus obtained were incubated in a 200 ml of half saturated sodium acetate, pH 8 at room temperature for 2–4 hours. 20 ml of acetic anhydride was slowly added in 4 to 8 hours to the sodium acetate solution containing the collagen particles while the pH of the solution was maintained at about 8 by adjusting with 1M NaOH. The acetylated collagen particles were then extensively washed with deionized, distilled water and air dried until use.

The net charge of the acetylated collagen particles from various batches was determined by the same method described in Example 1 above, and found to range between −40 moles/mole to −100 moles/mole.

EXAMPLE 3

Preparation of Collagen Particles

Collagen particles were prepared in a manner identical to that described in Example 1 above.

Alteration of Net Charge Density to −100−−200 moles/mole

Ten grams of collagen particles thus obtained were incubated in 200 ml of 3% sodium bicarbonate solution overnight at room temperature. A quantity of 5 grams of finely powered succinic anhydride was added gradually over a period of 4 to 8 hours with agitation. The system was held in the pH range 8–8.5 by gradual addition of 1M NaOH. The stirring was continued for a further 4 to 8 hours. The succinylated collagen was then extensively washed in deionized, distilled water, air dried, and stored until use.

The net charge of the succinylated collagen particles from various batches was determined by the same method described in Example 1 above, and found to range between −100 moles/mole to −200 moles/mole.

EXAMPLE 4

Preparation of Collagen Particles

Collagen particles were prepared in a manner identical to that described in Example 1 above.

Alteration of Net Charge Density to +40−+250 moles/mole

Ten grams of collagen particles thus obtained were incubated in 500 ml of methyl alcohol in the presence of 0.1N HCl, at room temperature for 24 hours. The methylated collagen was rinsed in several changes of methanol and air dried.

The net charge of the methylated collagen particles from various batches was determined by the same method described in Example 1 above, and found to range between +40 moles/mole to +250 moles/mole.

EXAMPLE 5

Delivery of Bone Morphogenetic Protein 2,000 μg of bone morphogenetic protein ("BMP") were first uniformly mixed in 1 ml of a neutral saline solution. One gram of the collagen particles from Example 1 was then mixed with the BMP solution (dissolved in 1 ml of distilled water). An additional 1 ml of the saline solution was slowly added to the mixture to obtain a paste-like material.

The BMP-containing paste-like material was administered to adult Beagle dogs according to the following procedures: The lumbar spine sites were prepped and draped according to standard surgical procedures to expose the spinous processes, dorsal vertebral laminas and adjacent facets. The surfaces of the spinous processes, dorsal laminae and facets were decorticated with a high speed burr to expose fresh bleeding bone. The thoroughly mixed paste-like matrices were inserted into decorticated laminae sites to promote spine fusion.

Other Embodiments

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

For example, collagen particles with a very high net charge density (e.g., −1,000 or +1,000 moles/mole) can be obtained using a polyanionic or polycationic polymer in manners described above under the subheading Detailed Description of the Invention. Such particles, their manufacture, and their use are also within the scope of this invention under the doctrine of equivalents.

What is claimed is:

1. A collagen-based delivery matrix comprising collagen particles, wherein each of the collagen particles in said delivery matrix has a diameter between 5 μm and 850 μm, and, when suspended in an aqueous solution at a pH of about 7.0, has a net charge density between −20 moles/mole collagen and −500 moles/mole collagen.

2. The collagen delivery matrix of claim 1, wherein each of the collagen particles in said delivery matrix has a net charge density between −40 moles/mole collagen and −400 moles/mole collagen.

3. The collagen delivery matrix of claim 2, wherein each of the collagen particles in said delivery matrix has a net charge density between −100 moles/mole collagen and −300 moles/mole collagen.

4. The collagen delivery matrix of claim 1, wherein each of the collagen particles in said delivery matrix has a diameter between 15 μm and 600 μm.

5. The collagen delivery matrix of claim 4, wherein each of the collagen particles in said delivery matrix has a net charge density between −40 moles/mole collagen and −400 moles/mole collagen.

6. The collagen delivery matrix of claim 5, wherein each of the collagen particles in said delivery matrix has a net charge density between −100 moles/mole collagen and −300 moles/mole collagen.

7. A collagen-based delivery matrix comprising collagen particles, wherein each of the collagen particles in said delivery matrix has a diameter between 5 μm and 850 μm, and, when suspended in an aqueous solution at a pH of about 7.0, has a net charge density between +20 moles/mole collagen and +250 moles/mole collagen.

8. The collagen delivery matrix of claim 7, wherein each of the collagen particles in said delivery matrix has a net charge density between +50 moles/mole collagen and +200 moles/mole collagen.

9. The collagen delivery matrix of claim 8, wherein each of the collagen particles in said delivery matrix has a net charge density between +100 moles/mole collagen and +160 moles/mole collagen.

10. The collagen delivery matrix of claim 7, wherein each of the collagen particles in said delivery matrix has a diameter between 15 μm and 600 μm.

11. The collagen delivery matrix of claim 10, wherein each of the collagen particles in said delivery matrix has a net charge density between +50 moles/mole collagen and +200 moles/mole collagen.

12. The collagen delivery matrix of claim 11, wherein each of the collagen particles in said delivery matrix has a net charge density between +100 moles/mole collagen and +160 moles/mole collagen.

13. A method of preparing collagen particles for a collagen delivery matrix, which method comprises:
    fragmenting a collagen preparation to form collagen particles; and
    chemically modifying the particles for use in said collagen delivery matrix so that each of the particles, when suspended in an aqueous solution at a pH of about 7.0, has a net charge density between −20 moles/mole collagen and −500 moles/mole collagen or between +20 moles/mole collagen and +250 moles/mole collagen.

14. The method of claim 13, further comprising, either before or after the modifying step, selecting collagen particles for said delivery matrix which have diameters between 5 μm and 850 μm.

15. The method of claim 14, wherein collagen particles with diameters between 15 μm and 600 μm are selected for said delivery matrix.

16. A method of using collagen particles comprising mixing the collagen particles, a bioactive agent, and an aqueous solution to form a paste-like material, wherein each of the particles has a diameter between 5 μm and 850 μm, and, when suspended in an aqueous solution at a pH of about 7.0, has a net charge density between −20 moles/mole collagen and −500 moles/mole collagen or between +20 moles/mole collagen and +250 moles/mole collagen.

17. The method of claim 16, wherein each of the collagen particles has a diameter between 15 μm and 600 μm.

18. The method of claim 17, further comprising delivering the paste-like material to a subject to be treated with the bioactive agent.

19. The method of claim 18, wherein the delivering step is effected with a syringe.

20. The method of claim 18, wherein the delivering step is effected with a cannula.

21. The method of claim 18, wherein the delivering step is effected with a catheter.

22. The method of claim 18, wherein the delivering step is effected by surgical implantation.

* * * * *